(12) United States Patent
Dudee

(10) Patent No.: US 12,035,972 B2
(45) Date of Patent: Jul. 16, 2024

(54) TREPHINATION APPARATUS AND METHOD

(71) Applicant: Jitander Dudee, Lexington, KY (US)

(72) Inventor: Jitander Dudee, Lexington, KY (US)

(*) Notice: Subject to any disclaimer, the term of this patent is extended or adjusted under 35 U.S.C. 154(b) by 865 days.

(21) Appl. No.: 17/062,684

(22) Filed: Oct. 5, 2020

(65) Prior Publication Data
US 2021/0100687 A1    Apr. 8, 2021

Related U.S. Application Data

(60) Provisional application No. 62/910,018, filed on Oct. 3, 2019.

(51) Int. Cl.
| | | |
|---|---|---|
| A61B 3/135 | (2006.01) | |
| A61B 3/00 | (2006.01) | |
| A61B 17/3205 | (2006.01) | |
| A61F 2/16 | (2006.01) | |
| A61F 9/007 | (2006.01) | |
| A61F 2/48 | (2006.01) | |

(52) U.S. Cl.
CPC .......... *A61B 3/135* (2013.01); *A61B 3/0008* (2013.01); *A61B 3/0033* (2013.01); *A61B 3/0075* (2013.01); *A61B 17/32053* (2013.01); *A61F 2/1618* (2013.01); *A61F 2/1632* (2013.01); *A61F 2/164* (2015.04); *A61F 2/1651* (2015.04); *A61F 2/1656* (2013.01); *A61F 9/00754* (2013.01); *A61F 9/00763* (2013.01); *A61F 2002/16901* (2015.04); *A61F 2/48* (2021.08)

(58) Field of Classification Search
CPC .......... A61B 17/32053; A61F 9/00754; A61F 9/00763
See application file for complete search history.

(56) References Cited

U.S. PATENT DOCUMENTS

| | | | | |
|---|---|---|---|---|
| 4,744,362 | A * | 5/1988 | Grundler | ................ A61B 34/70 606/166 |
| 5,092,874 | A | 3/1992 | Rogers | |
| 5,464,417 | A * | 11/1995 | Eick | ........................ A61F 9/007 606/166 |
| 5,649,944 | A * | 7/1997 | Collins | ..................... A61F 2/14 606/166 |
| 6,425,905 | B1 | 7/2002 | Guimaraes et al. | |
| 6,689,147 | B1 * | 2/2004 | Koster, Jr. | .............. A61B 17/11 606/151 |
| 2010/0152754 | A1 * | 6/2010 | Weston | ................... A61F 9/013 606/166 |

* cited by examiner

*Primary Examiner* — Richard G Louis
(74) *Attorney, Agent, or Firm* — Black McCuskey

(57) ABSTRACT

A trephination apparatus can include a first member, a blade, and a second member. The first member can include a through-aperture and a first internal chamber. The first member can also include opening to the first internal chamber that can surround the through-aperture in a plane. The blade can have an outwardly-facing male profile at least partially matching the through-aperture and have a cutting edge. The second member can include a first body sized to be received in the through-aperture with the blade. The blade can be positionable between the first body and the female profile at the second opening. The second member can also include a second internal chamber with an opening extending about the aperture axis in the plane with an opening to the first internal chamber.

20 Claims, 8 Drawing Sheets

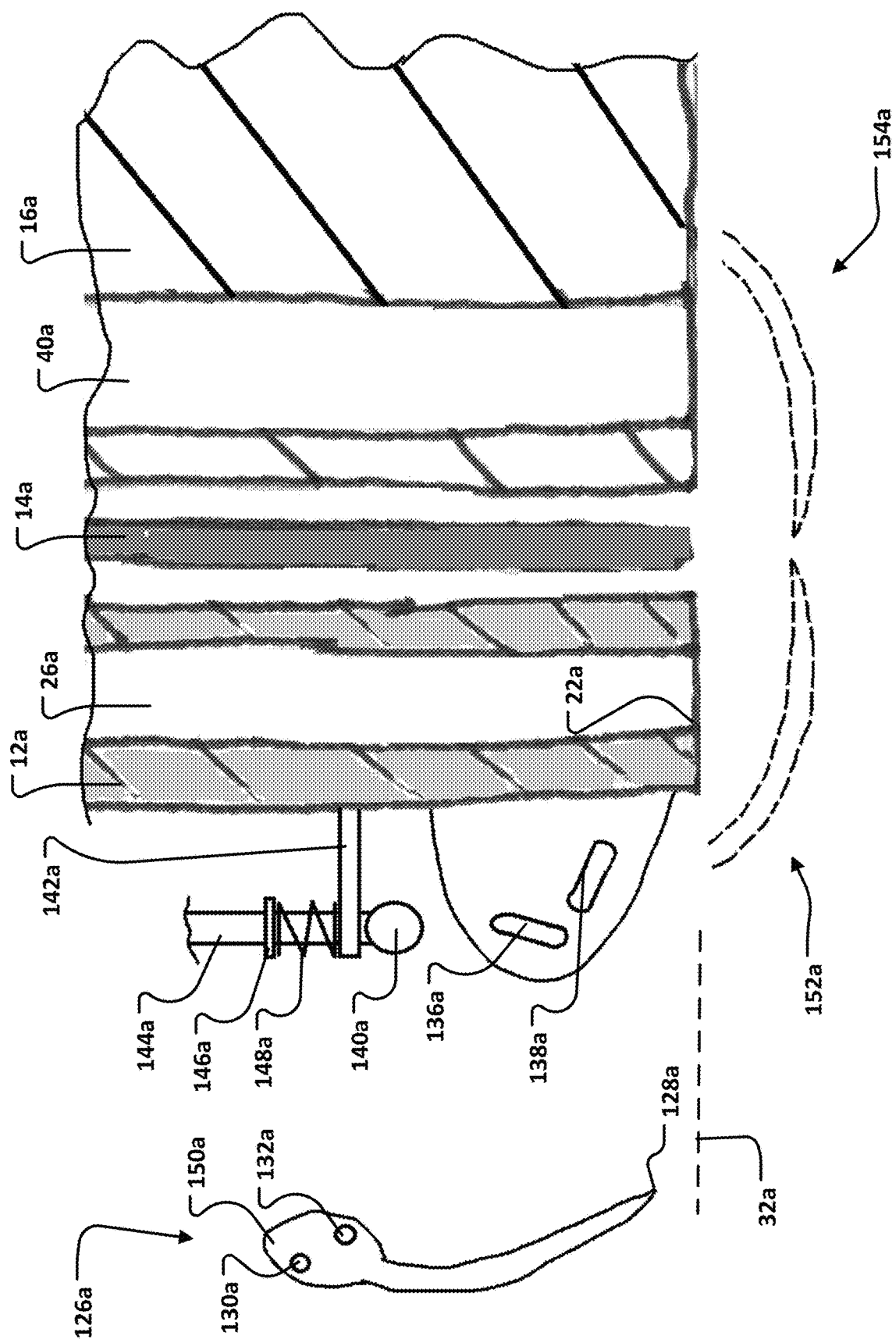

TREPHINATION APPARATUS AND METHOD

CROSS-REFERENCE TO RELATED APPLICATIONS

This application claims the benefit of U.S. Provisional Patent Application Ser. No. 62/910,018 for EYE CARE, filed on 2019 Oct. 3, which is hereby incorporated by reference in its entirety.

BACKGROUND

1. Field

The present disclosure relates to devices or appliance for use in operative surgery upon the body or in preparation for operative surgery, together with devices designed to assist in operative surgery (USPC class 606), and more particularly to cutting means or a means to direct the path of a cutting means used in a surgical procedure upon the anterior, external transparent layer of an eye (subclass 166).

2. Description of Related Prior Art

U.S. Pat. No. 5,092,874 discloses a penetrating keratoplasty trephination press, an instrument for facilitating the accurate trephination of donor corneal tissue. The instrument can easily accommodate different sizes of trephines and provides for proper and accurate positioning of the donor tissue to ensure a proper central cut of the tissue. The instrument utilizes an integral base and stand that supports a moveable piston which drives the trephine through the tissue carried by a cutting block supported on the base.

U.S. Pat. No. 6,425,905 discloses a method and apparatus for facilitating removal of a corneal graft. The invention relates to an artificial chamber that can support and pressurize a donor cornea to extract a corneal graft. The artificial chamber has a stationary stem that is adapted to support a cornea. The stem has an inner channel that allows air to pressurize the cornea. The artificial chamber has an outer cap that can be moved in a downward direction to secure the cornea. The cap has an opening that exposes a portion of the cornea to allow for the extraction of a corneal graft. The outer cap is attached to an outer sleeve that is moved by rotation of a cam. The chamber includes a spring that exerts a clamping force onto the cornea. The clamping force can be adjusted by rotating an adjustment wheel. The adjustable spring force allows an operator to set a desired clamping force that is then repeated for each grafting procedure.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A trephination apparatus can include a first member, a blade, and a second member. The first member can include a through-aperture extending between a first opening and second opening spaced from the first opening. The through-aperture can be centered on an aperture axis and can define a female profile at the second opening in a plane normal to the aperture axis. The first member can also include a first internal chamber. The first member can also include a third opening to the first internal chamber. The first member can also include a fourth opening to the first internal chamber spaced from the third opening. The fourth opening can surround the second opening in the plane. The blade can have an outwardly-facing male profile at least partially matching the female profile and received in the through-aperture. The blade can also define a first cutting edge. The second member can include a first body sized to be received in the through-aperture with the blade. The blade can be positionable between the first body and the female profile at the second opening. The second member can also include a second internal chamber. The second member can also include a fifth opening to the second internal chamber. The second member can also include a sixth opening to the second internal chamber spaced from the fifth opening. The sixth opening can extend about the aperture axis in the plane with the fourth opening.

BRIEF DESCRIPTION OF THE DRAWINGS

The detailed description set forth below references the following drawings:

FIG. 10 is a detail view of another embodiment of the present disclosure.

DETAILED DESCRIPTION

Figure 1:
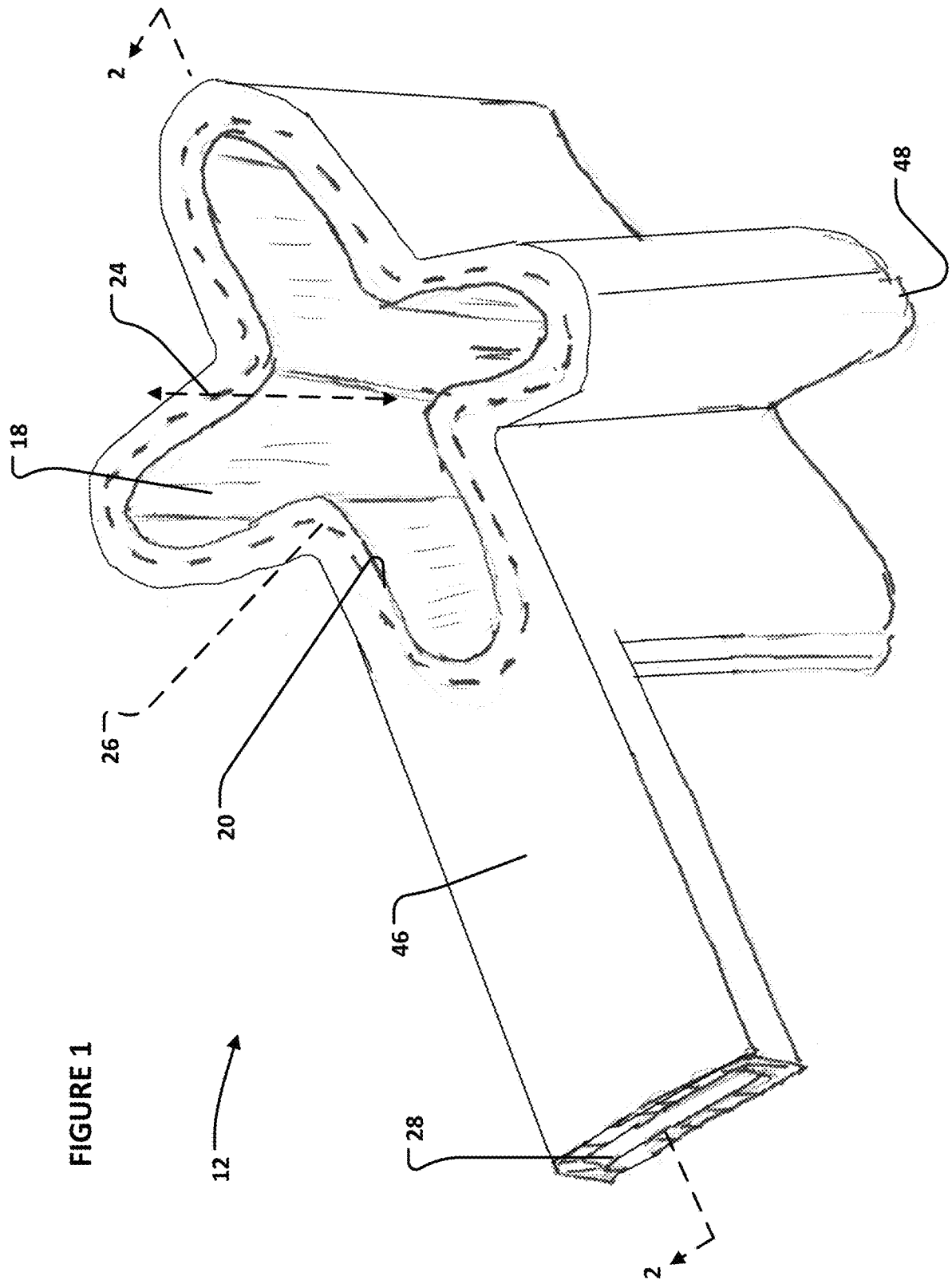
FIG. 1 is an isometric view of a first member of an exemplary embodiment of a trephination apparatus according to the present disclosure.
Figure 2:
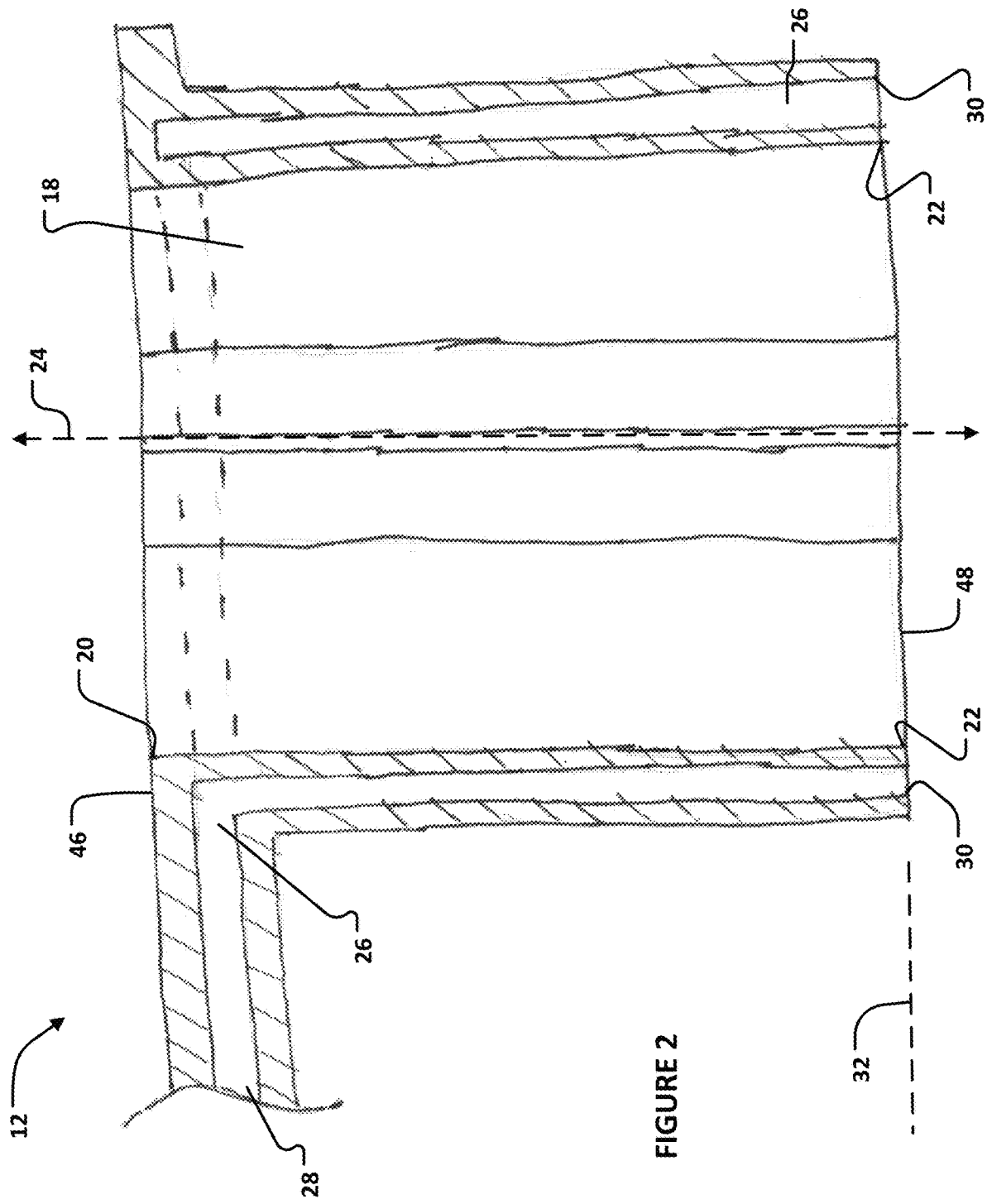
FIG. 2 is a cross-section through section lines 2-2 in FIG. 1.

A plurality of different embodiments of the present disclosure is shown in the Figures of the application. Similar features are shown in the various embodiments of the present disclosure. Similar features across different embodiments have been numbered with a common reference numeral and have been differentiated by an alphabetic suffix. Also, to enhance consistency, the structures in any particular drawing share the same alphabetic suffix even if a particular feature is shown in less than all embodiments. Similar features are structured similarly, operate similarly, and/or have the same function unless otherwise indicated by the drawings or this specification. Furthermore, particular features of one embodiment can replace corresponding features in another embodiment or can supplement other embodiments unless otherwise indicated by the drawings or this specification.

The present disclosure, as demonstrated by the exemplary embodiments described below, can provide an instrument to allow grasping of a periphery of a corneal recipient wound.

One or more embodiments of the present disclosure provide a double vacuum ring which avoids the problem of the anterior chamber of the eye collapsing as soon as the trephine blade enters the anterior chamber. Collapsing can occur when anterior chamber fluid is sucked up into a vacuum chamber. A further advantage of a double vacuum ring is that the vacuum ring can be left in situ to support the host tissue after the central diseased button is removed. One or more embodiments of the present disclosure can be a modular assembly so that central and outer vacuum rings are independent of each other and also independent of the assembly driving the cutting surface into the cornea.

A trephination apparatus 10 can include a first member 12, a blade 14, and a second member 16. The first member 12 can include a through-aperture 18 extending between a first opening 20 and second opening 22 spaced from the first opening 20. The through-aperture 18 can be centered on an aperture axis 24 and can define a female profile at the second opening 22 in a plane normal to the aperture axis 24. The plane is referenced at 32. In the exemplary embodiment, the profile of the aperture 18 is the same at both openings 20, 22 so the view of the opening 20 in FIG. 1 also shows the shape of the opening 22. The exemplary female profile defined at the opening 22 is thus multilobular in the plane 32. In the exemplary embodiment, the female profile defined at the opening 22 is constant between the first end 46 and the second end 48. The exemplary first member 12 extends along the aperture axis 24 between a first end 46 and a second end 48. The exemplary second end 48 is at the plane 32 with the second opening 22.

The first member 12 can also include a first internal chamber 26. An internal boundary of the first internal chamber 26 is referenced by dash line in FIG. 1. The first member 12 can also include a third opening 28 to the first internal chamber 26. The first member 12 can also include a fourth opening 30 to the first internal chamber 26 spaced from the third opening 28. The fourth opening 30 can surround the second opening 22 in the plane 32. It is noted that, in the exemplary embodiment of the present disclosure, the cross-sectional view in FIG. 3, as between the openings 22, 30 is the same about the entire axis 24. The exemplary first internal chamber 26 is accessible only through the third opening 28 and the fourth opening 30. The blade 14 does not extend through the first internal chamber 26 in the exemplary embodiment of the present disclosure.

Figure 4:
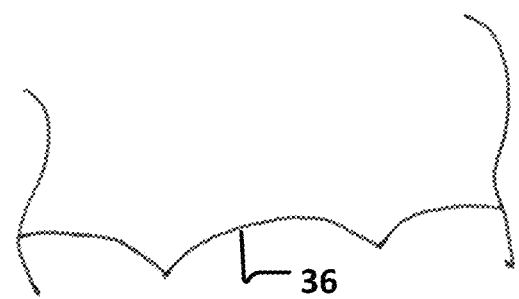
FIG. 4 is a detail view of a cutting edge of the blade.

The blade 14 can have an outwardly-facing male profile 34 at least partially matches the female profile defined at the opening 22. In the exemplary embodiment, the profile 34 is multilobular like the female profile of the opening 22. The exemplary blade 14 is received in the through-aperture 18. The blade 14 can also define a first cutting edge 36. The exemplary cutting edge 36 extends around the entire axis 24. The exemplary cutting edge 36 has an undulated profile, as shown in FIG. 4.

The second member 16 can include a first body 38 sized to be received in the through-aperture 18 with the blade 14. The blade 14 can be positionable between the first body 38 and the female profile defined at the second opening 22. The second member 16 can also include a second internal chamber 40. The second member 16 can also include a fifth opening 42 to the second internal chamber 40. The second member 16 can also include a sixth opening 44 to the second internal chamber 40 spaced from the fifth opening 42. The sixth opening 44 can extend about the aperture axis 24 in the plane 32 with the fourth opening 30. The exemplary sixth opening 44 extends coextensively with the fourth opening 30, fully around the axis 24. The exemplary second internal chamber 40 is as accessible only through the fifth opening 42 and the sixth opening 44. The blade 14 does not extend through the second internal chamber 40 in the exemplary embodiment of the present disclosure.

Figure 3:
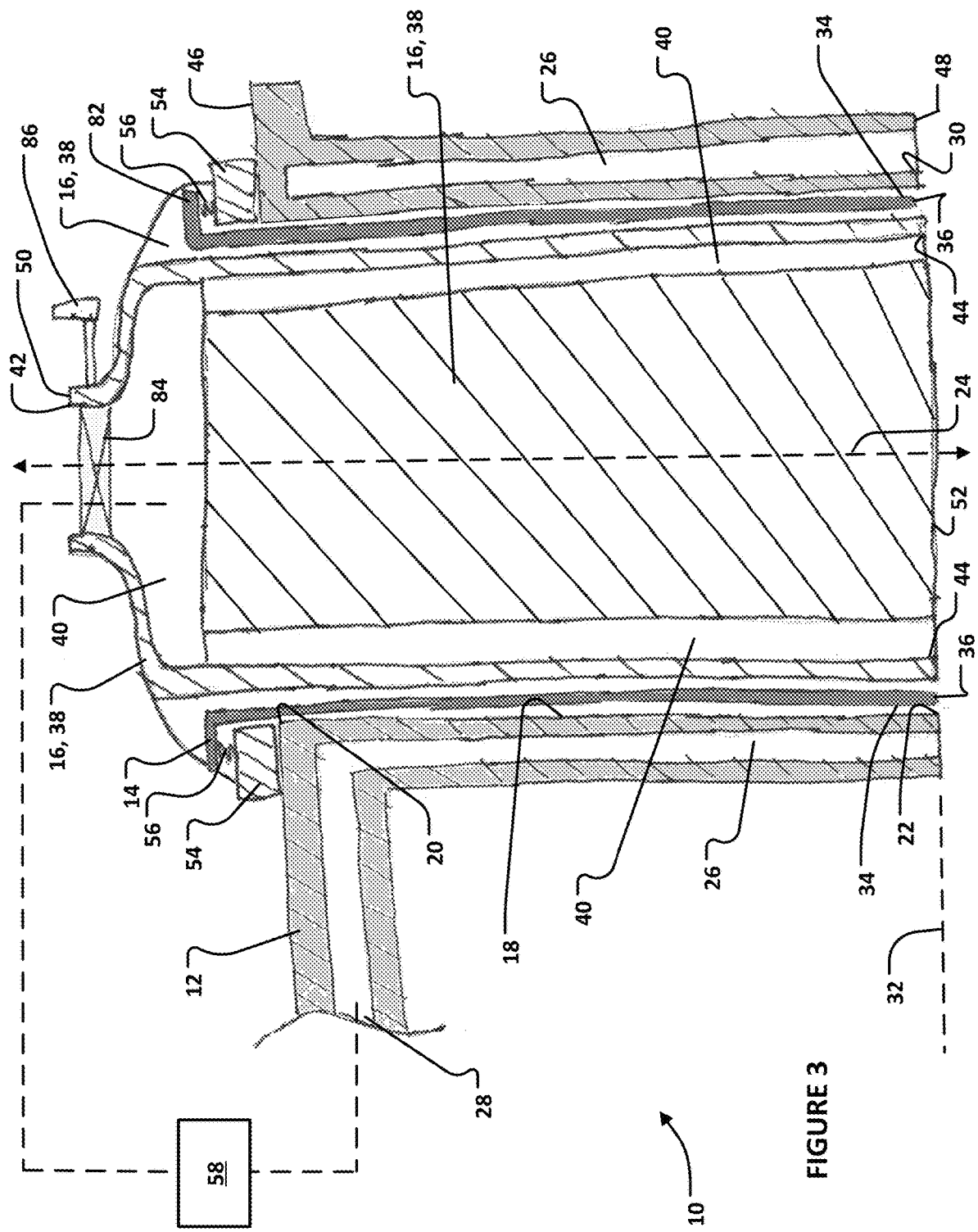
FIG. 3 is a cross-section of a blade and of a second member of the exemplary embodiment, taken in the same plane as FIG. 2 when the first member, blade and second member are engaged together.

The exemplary second member 16 extends along the aperture axis 24 between a third end 50 and a fourth end 52 when the first body 38 is received in the through-aperture 18, as shown in FIG. 3. The exemplary fourth end 52 is at the plane 32 with the second opening 22 and the second end 48, whereby the exemplary fourth opening 30 and the exemplary sixth opening 44 are substantially coplanar.

The exemplary second member 16 includes a protuberance 54 projecting further away from the aperture axis 24 than the first body 38 when the first body 38 is received in the through-aperture 18. The exemplary protuberance 54 abuts the first end 46 when the first body 38 is received in the through-aperture 18, as shown in FIG. 3. The engagement between the protuberance 54 and the first end 46 limits movement of the first body 38 into the through-aperture 18.

The exemplary blade 14 is moveably mounted on the second member 16. The exemplary blade 14 extends at least partially about the first body 38 and about the aperture axis 24 and is moveable between a retracted position and an extended position. FIG. 3 shows the blade 14 in the retracted position. Relative to the view of FIG. 3, the blade 14 would be lower when in the extended position. The exemplary cutting edge 36 is positioned between the first end 46 and the plane 32 when the blade 14 is in the retracted position. When the blade 14 is in the extended position, the plane 32 is between at least part of the first cutting edge 36 and the first end 46. At least one spring 56 can be positioned between the second member 16 and the blade 14 to bias the blade 14 to the retracted position.

Referring now to FIG. 3, the device 10 can also include at least one air-drawing device 58 that is connectable with at least one of the first opening 20 and the third opening 42. The device 58 can draw air through one or both of the first internal chamber 26 and the second internal chamber 40 to generate a vacuum in one of the first internal chamber 26 and the second internal chamber 40 when the fourth opening 30 or the sixth opening 44 is abutting another structure and thereby closed. The dashed lines emanating the device 58 represent air lines.

Figure 5:
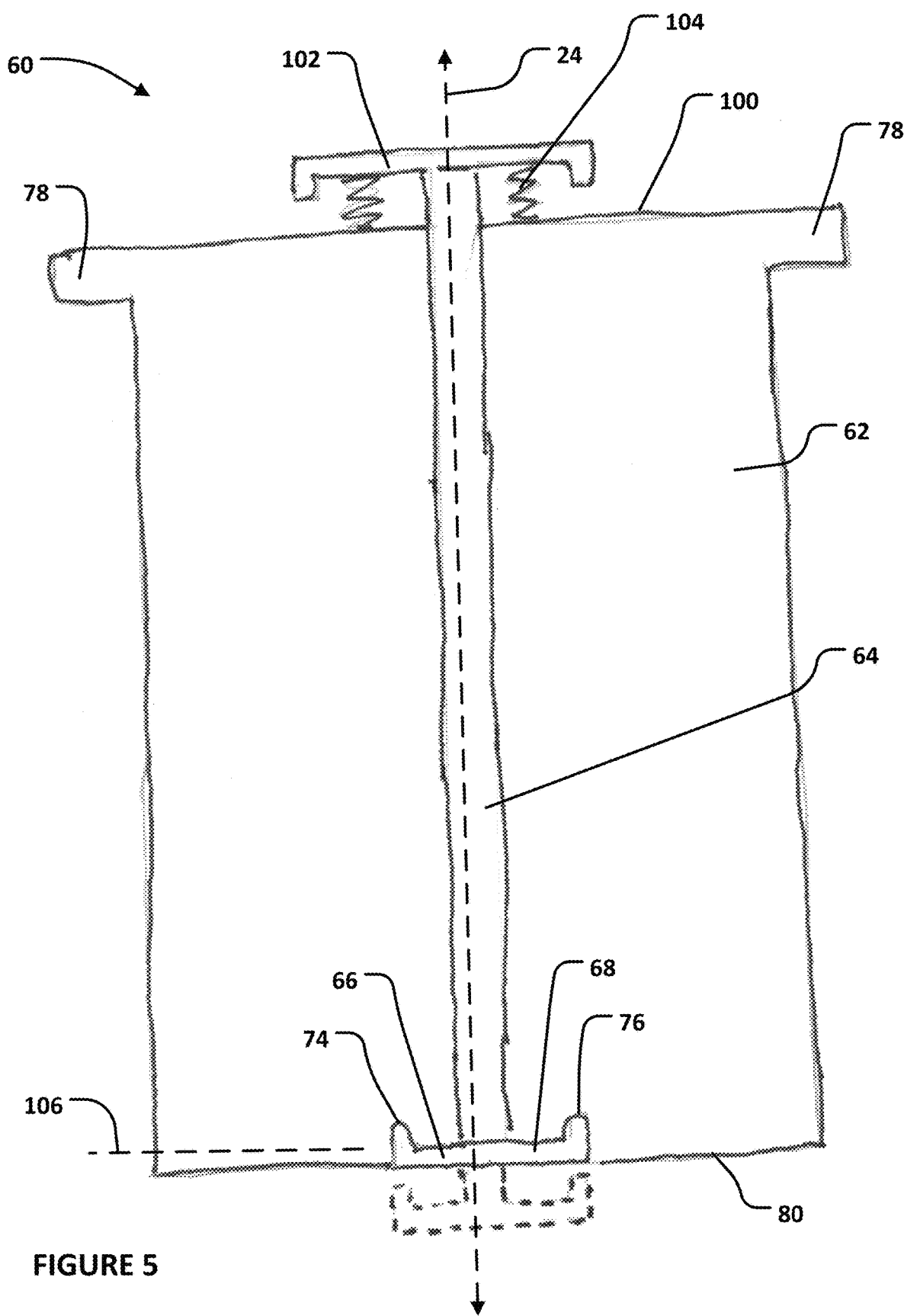
FIG. 5 is a cross-section of a cutting tool of the exemplary embodiment, taken in the same plane as FIG. 2 when the first member and cutting tool are engaged together.

Referring now to FIG. 5, the device 10 can also include a cutting tool 60. The cutting tool 60 can include a second body 62 sized to be received in the through-aperture 18 when the blade 14 and the second member 16 are not positioned in the through-aperture 18. The cutting tool 60 can also include a shaft 64 positioned in the second body 62 and configured to rotate relative to the second body 62. The exemplary cutting tool 60 also includes arms 66, 68, 70, 72 mounted on and projecting away from the shaft 64. The exemplary cutting tool 60 also include cutting edges, one each respectively mounted on the arms. Cutting edges 74 and 76, respectively mounted on arms 66, 68, are shown in FIG. 5. It is noted that the structures shown in FIG. 5 are in cross-section (despite the lack of cross-hatching) in a plane similar to the plane of view of FIG. 3. The exemplary cutting edges 74, 76 are both directed along the aperture axis 24 when the second body 62 is received in the through-aperture 18. In other words, in the exemplary embodiment, the exemplary cutting edges 74, 76 point upward.

The exemplary cutting tool 60 includes a protuberance 78 projecting further away from the aperture axis 24 than the second body 62 when the second body 62 is received in the through-aperture 18. The protuberance 78 abuts the first end 46 when the second body 62 is received in the through-aperture 18 and limits movement of the second body 62 into the through-aperture 18.

The exemplary shaft 64 is mounted in the second body 62 for rectilinear movement along the aperture axis 24 when the second body 62 is received in the through-aperture 18. Thus, the arm 66 and the second cutting edge 36 are also rectilinearly moveable along the aperture axis 24. The exemplary shaft 64 is moveable between a retracted position and an extended position. FIG. 5 shows, in dash line, the position of the arms 66 and 68 and the cutting edges 74 and 76 when the shaft 64 is in the extended position.

The second body 62 defines a bottom edge 80 positionable in the plane 32 when the second body 62 is received in the through-aperture 18. Thus, the bottom edge 80 would be laterally aligned with the second end 48 when the cutting tool 60 is received in the first member 12. The second body 62 also defines a cavity recessed from the bottom edge 80. The cavity is shaped to correspond to a shape of the arms and of the second cutting edges. In FIG. 5, the profile of the arms 66, 68 and cutting edges 74, 76 is also the profile of the cavity. As a result, the arms 66, 68 and the cutting edges 74, 76 are received in the cavity when the shaft 64 is in the retracted position and are spaced from the cavity when the shaft 64 is in the extended position.

In an exemplary method of removing a portion of a cornea of an eye with the trephination apparatus 10 includes placing the first member 12 on the cornea of the eye. The first member 12 can be placed so that the fourth opening 30 is closed by the cornea. The method can also include inserting the first body 38 of the second member 16 into the through-aperture 18 and on the cornea. The second member 16 can be placed so that the sixth opening 44 is closed by the cornea. The second member 16 can be inserted into the aperture 18 until the protuberance 54 rests on the first end 46.

The method can also include activating the device 58 and applying a suction to the first opening 20 and the fifth opening 42. This can create a vacuum in the first internal chamber 26 and the second internal chamber 40. Respective portions of the cornea are drawn toward the first opening 20 and the fifth opening 42 and held.

The method can also include moving the blade 14 along the aperture axis 24, within the space between the first member 12 and the second member 16, until the blade 14 pierces the cornea. This detaches the portion of the cornea that extends from the axis 24, radially outward, to the cut edge, from a remainder of the cornea. It is noted that the exemplary blade 14 can be moved by pressing down on a handle portion 82 of the blade 14, against the force of the spring 56. It is also noted that the shape of the blade 14 shown in FIG. 3 and the approach to moving the blade 14 are exemplary and not limiting.

It is noted that in one or more embodiments of the present disclosure, the second member 16 can include a valve 84, shown schematically in FIG. 3. After the cornea has been cut, the valve 84 can be closed to retain the vacuum in the chamber 40 and thus retain the detached portion of the cornea on the second member 16. FIG. 3 shows a lever 86 for opening and closing the valve 84.

The exemplary device 10 can also be utilized in preparing the cornea of the recipient of the donor cornea portion. In a method of utilizing the device 10, the damaged/diseased portion of the cornea can be removed following the process described above. The first member 12 can remain placed on the cornea, with the fourth opening 30 closed by the cornea, and the vacuum in the chamber 26 maintained. The method can also include inserting the second body 62 of the cutting tool 60 into the through-aperture 18 until the second body 62 rests on the first member 12. This can occur when the protuberance 78 rests on the first end 46.

The process can then include moving the shaft 64 relative to the second body 62, rectilinearly downward along the aperture axis 24. This can space the arms 66, 68 and the cutting edges 74, 76 from the second body 62. This is shown in dash line in FIG. 5. The shaft 64, arms 66, 68, and cutting edges 74, 76 can be sized so that the cutting edges 74, 76 will be positioned below the edge of the cornea that this held at the opening 30.

Figure 6:
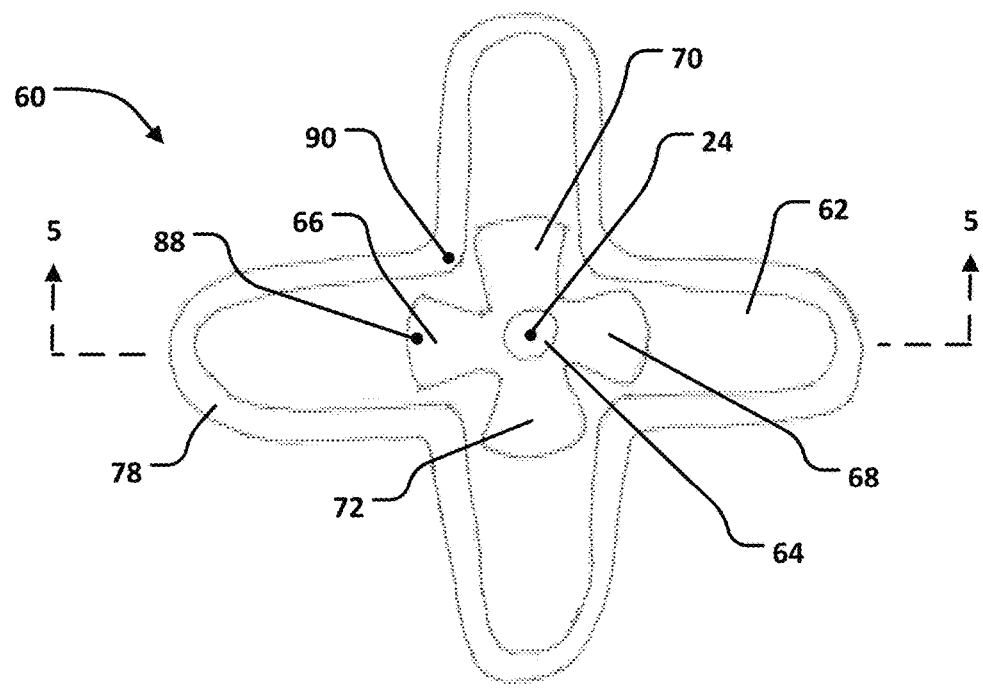
FIG. 6 is a bottom view of the cutting tool shown in cross-section in FIG. 5.

Next, the shaft 64 can be rotated relative to the second body 62, about the aperture axis 24. The shaft 64 can be rotated to position the cutting edges 74, 76 under a portion of the recipient's cornea and also under a portion of the first member 12. FIG. 6 is a bottom view of the cutting tool 60. The cutting edge 74 is not visible, but is located generally at the point 88. When the shaft 64 is rotated approximately forty-five degrees clockwise (based on the orientation of FIG. 6), the cutting edge 74 will be located generally at the point 90. Point 90 will be below the recipient's cornea and also under a portion of the first member 12.

After the shaft 64 has been rotated, the shaft 64 can be moved relative to the second body 62, rectilinearly upward along the aperture axis 24, to pierce the recipient's cornea with the cutting edge 74. The exemplary first member 12 and exemplary cutting tool 60 are sized/configured so that the cutting edge 74 abuts a place on the second end 48 of the first member 12 in the plane 32 when (a) the second body 62 is received in the through-aperture 18, (b) the shaft 64 is rectilinearly spaced from the retracted position as described immediately above, and (c) the second cutting edge 36 is rotated about the aperture axis 24 away from the cavity as described above.

Figure 7:
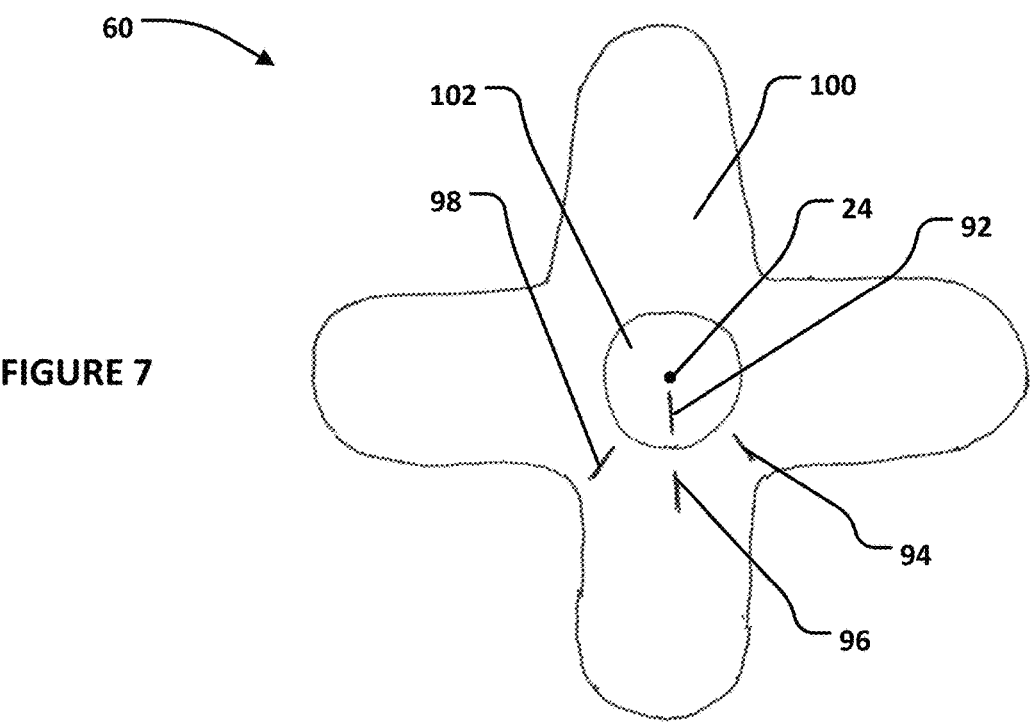
FIG. 7 is a top view of the cutting tool shown in cross-section in FIG. 5.

FIG. 7 is a top view of the cutting tool 60 and shows how the cutting tool 60 can include markings to assist in the positioning of the cutting edge 74. The cutting tool 60 can include a graspable knob 102. Visual indicia or raised bumps, referenced at 92, 94, 96, 98, can be positioned on the knob 102 and a top surface 100 of the second body 62 to assist the user in moving the shaft 64. For example, alignment of the indicia 92 and 96 can indicate that the cutting edge 74 is positioned in the cavity or aligned with the cavity. When the indicia 92 and 96 are aligned, the knob 102 can be pressed down, against at least one spring such as spring 104, and rotated until the indicia 92 and 98 are aligned. The knob 100 can be slowly released, which allows the spring 104 to move the shaft 64 and cutting edge 74 upward.

The text above describes an operation is which cutting edge 74 pierces a portion of the cornea when the shaft 64 is moved rectilinearly upward. However, the first member 12 and cutting tool 60 can be sized/configured so that the cutting edge 74 does not fully project through the cornea. Instead of piercing, the cutting edge 74 could be limited in vertical movement so that it only forms a divot in the portion of the cornea held by the first member 12. In one or more other embodiments of the present disclosure, the cutting edge 74 could be limited in vertical movement and also rotated while slightly raised to form a channel or trench in the underside of the cornea.

Figure 8:
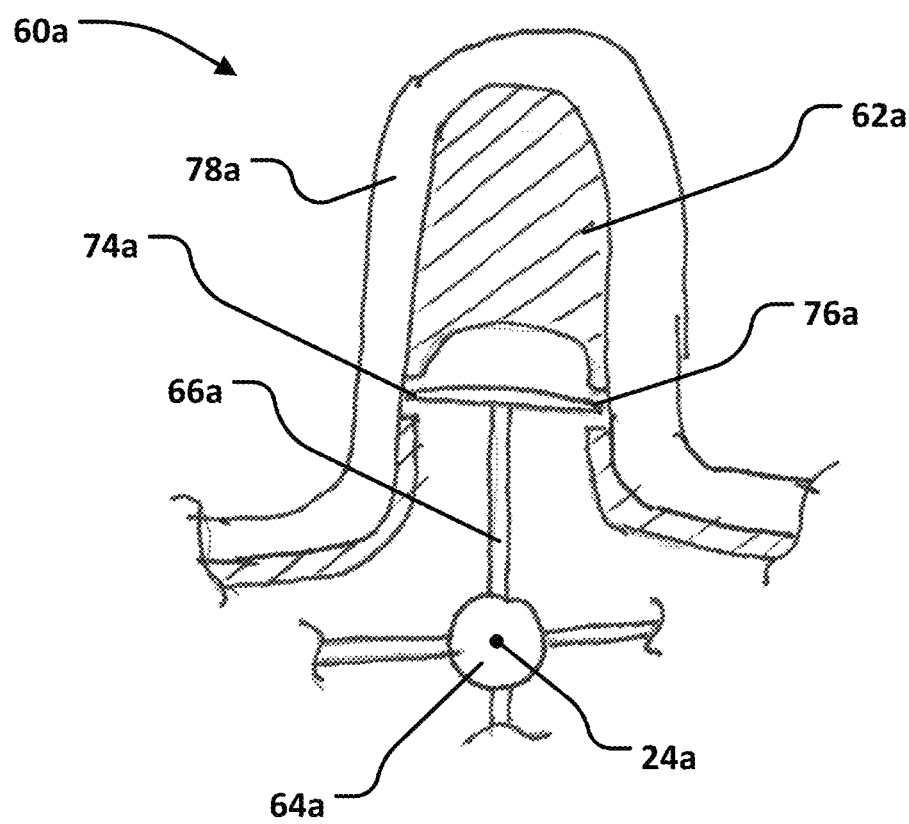
FIG. 8 is a partial cross-section of a cutting tool according to another exemplary embodiment of the present disclosure.

FIG. 8 shows an alternative embodiment of the present disclosure. FIG. 8 is a partial cross-section of a cutting tool according to another exemplary embodiment of the present disclosure. The view of FIG. 8 is in a plane that would be positioned as a plane 106 is positioned in FIG. 5, looking upward. A cutting tool 60a includes a second body 62a, a protuberance 78a, a shaft 64a. The shaft 64a extends along an axis 24a. An arm 66a extends from the shaft 64a. Cutting edges 74a, 76a are mounted on the arm 66a. The cutting edges 74a, 76a are directed transverse to the aperture axis 24. The shaft 64a can be rotated over a range of about sixty degrees to extend the cutting edges 74a, 76a through apertures in the second body 62a and form tunnels in the cornea.

It is noted that the exemplary embodiments include annular, ring-shaped openings through which to apply a vacuum to hold the cornea. In one or more other embodiments of the present disclosure, the various structures could define a pattern of individual circular openings through which to apply a vacuum.

Figure 9:
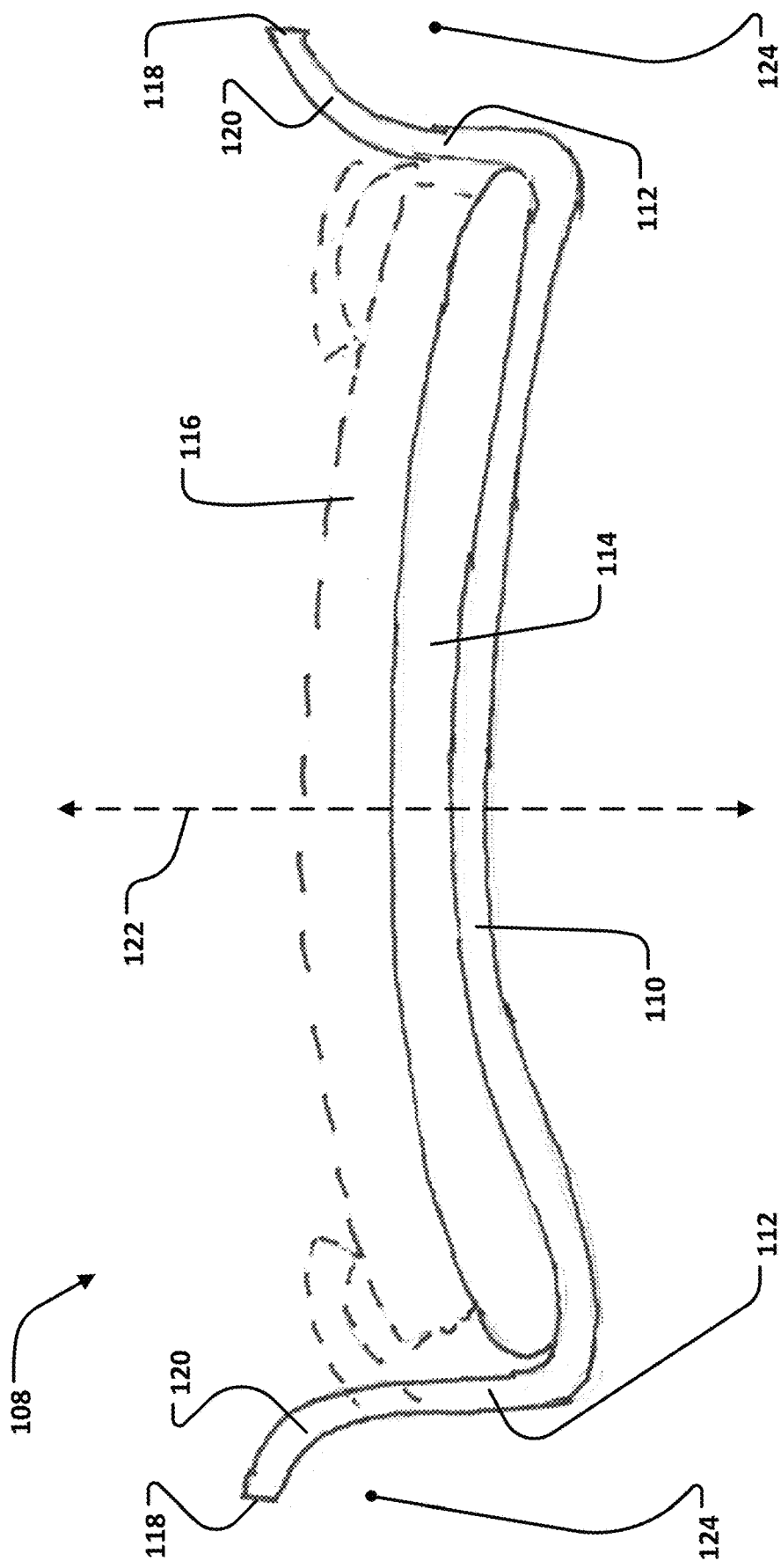
FIG. 9 is a cross-sectional view of a container for holding a portion of a cornea.

It was noted above that, in one or more embodiments of the present disclosure, a detached portion of a cornea could be held by the second member 16. FIG. 9 is a cross-sectional view of an alternative container 108 for holding a portion of a cornea. The container 108 can include a bottom wall 110 and a side wall 112. A quantity of fluid, referenced at 114 can be held in the container 108 for the portion of the cornea. The portion of the cornea is shown in dash line and referenced at 116. The side wall 112 extends from the bottom wall 110 to a distal end 118. Proximate to the distal end 118, the side wall 112 defines a shell-shape portion 120. The shell-shape portion 120 can have the shape of less than a full ring torus wherein the shell-shaped portion 120 extends three hundred and sixty degrees about a central axis 122 in the toroidal direction and extends no greater than one hundred and eighty degrees about a poloidal center of curvature, referenced at 124 in FIG. 9. After the portion 116 of the cornea is place in the container 108, the distal end 118 can be pressed toward the axis 122. This causes the shell 120 to invert such that the poloidal center of curvature moves toward the axis 122. The inverted shell 120 is shown in dash line. The inverted shell 120 can capture and hold the portion 116. The dimensions of the shell 114g can be selected in view of several references that disclose the mathematical relationships necessary for "snapping" as shown in FIGS. 22 and 23. These references include "Curvature-Induced Instabilities of Shells" by Pezzulla et al.

FIG. 10 is a detail view of another embodiment of the present disclosure. FIG. 10 includes details of the lower-left portion of FIG. 3. A first member 12a defines a first internal chamber 26a. A second member 16a defines a second internal chamber 40a. A blade 14a is positioned in a gap between the first member 12a and the second member 16a. A second opening 22a is defined in a plane 32a. The embodiment shown partially in FIG. 10 also includes structures for forming suture apertures in donor corneal tissue and in recipient corneal tissue. The suture apertures that are formed can be arcuate. Further, the suture apertures that are formed in the donor corneal tissue will align with the suture apertures that are formed in the recipient corneal tissue.

The following description applies to exemplary structures for forming the suture apertures and not to the only structures that can be applied. Also, the structures for forming the suture apertures in the recipient corneal tissue will be described. Identical structures that are mirrored relative to the described structures can be incorporated in the second member to form suture apertures in the donor corneal tissue.

The structures for forming the suture apertures in the recipient corneal tissue include a hook 126a. The hook 126a can be curved and define a point 128a. In operation, the point 128a can project below the plane 32a when the first member 12a is placed on the recipient's cornea. As a result, the hook 126a can pierce the recipient's cornea before the recipient's cornea is cut by the blade 14a.

It can be desirable to form a suture aperture that extends laterally through the cornea, toward the cut edge of the cornea. However, it can also be desirable to have the point 128a initially projecting downward so that the point 128a will pierce perpendicularly into the cornea. Thus, it can be desirable that the hook 126a proceed into the cornea with at least partial pivoting motion.

The exemplary hook 126a includes first and second guide pins 130a, 132a. The structures for forming the suture apertures in the recipient corneal tissue also include a bracket 134a fixed to the first member 12a proximate to the plane 32a. The bracket 134a defines slots 136a, 138a that respectively receive the guide pins 130a, 132a. It is noted that the hook 126a is shown in an exploded or unconnected condition to the bracket 134a in FIG. 10 to enhance the clarity of the structures.

The structures for forming the suture apertures in the recipient corneal tissue also include a hammer or cam 140a fixed to the first member 12a through a bracket 142a. A rod 144a extends from the cam 140a upward to a top surface of the first member 12a so that the rod 144a can be engaged by a user. A washer 146a is fixed on the rod 144a and a spring 148a is positioned between the washer 146a and the bracket 142a to bias the rod 144a and cam 140a upwards.

The hook 126a includes a head 150a that contacts the cam 140a and acts as a cam follower. When the rod 144a is directed downward by a user, the cam 140a urges the head 150a, and thus remainder of the hook 126a, downward. As shown in FIG. 10, the slots 136a, 138a do not extend parallel to one another. Thus, the slots 136a, 138a are shaped to induce partial pivoting motion of the hook 126a. The cooperation between the pin 130a and slot 136a will cause the head 150a to move substantially straight downward. The cooperation between the pin 132a and slot 138a will cause the head 150a to move downward and to the right (based on the perspective of FIG. 10). The hook 126a is thus guided in a complex motion that includes pivoting and rectilinear movement.

The rod 144a can be released by the user and the spring 148a will cause the hook 126a to be at least partially drawn out of the suture aperture. While not shown, the cam 140a and head 150a can be connected through a pin so that when cam 140a is urged upward by the spring 148a the hook 126a is also drawn upwardly. The shape of the suture aperture is shown in dash line and referenced at 152a. The shape of a suture aperture formed by similar structures mounted on the second member 16a is shown in dash line and referenced at 154a.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or sub-combinations that are disclosed herein is hereby unconditionally reserved. The use of the word "can" in this document is not an assertion that the subject preceding the word is unimportant or unnecessary or "not critical" relative to anything else in this document. The word "can" is used herein in a positive and affirming sense and no other motive should be presumed. More than one "invention" may be disclosed in the present disclosure; an "invention" is defined by the content of a patent claim and not by the content of a detailed description of an embodiment of an invention.

What is claimed is:

1. A trephination apparatus comprising:
a first member with:
a through-aperture extending between a first opening and second opening spaced from said first opening, said through-aperture centered on an aperture axis and defining a female profile at said second opening in a plane normal to said aperture axis,
a first internal chamber,
a third opening to said first internal chamber, and
a fourth opening to said first internal chamber spaced from said third opening, said fourth opening surrounding said second opening in the plane; and
a blade having an outwardly-facing male profile at least partially matching said female profile and sized to be received in said through-aperture and also defining a first cutting edge; and
a second member with:
a first body sized to be received in said through-aperture with said blade, said blade positionable between said first body and said female profile at said second opening,
a second internal chamber,
a fifth opening to said second internal chamber, and
a sixth opening to said second internal chamber spaced from said fifth opening, said sixth opening extending about said aperture axis in the plane with said fourth opening.

2. The trephination apparatus of claim 1 wherein said first internal chamber is further defined as accessible only through said third opening and said fourth opening.

3. The trephination apparatus of claim 1 wherein said second internal chamber is further defined as accessible only through said fifth opening and said sixth opening.

4. The trephination apparatus of claim 1 wherein:
said first member extends along said aperture axis between a first end and a second end, said second end at said plane with said second opening; and
said second member, when said first body is received in said through-aperture, extends along said aperture axis between a third end and a fourth end, said fourth end at said plane with said second opening and said second end, whereby said fourth opening and said sixth opening are substantially coplanar.

5. The trephination apparatus of claim 4 wherein said second member further comprises:
at least one protuberance projecting further away from said aperture axis than said first body when said first body is received in said through-aperture, said protuberance abutting said first end when said first body is received in said through-aperture and limiting movement of said first body into said through-aperture.

6. The trephination apparatus of claim 5 wherein said blade is further defined as moveably mounted on said second member, extending at least partially about said first body and about said aperture axis, said blade moveable between a retracted position and an extended position, said first cutting edge positioned between said first end and said plane when said blade is in said retracted position, and said plane between at least part of said first cutting edge and said first end and when said blade is in said extended position.

7. The trephination apparatus of claim 1 wherein said female profile is further defined as multilobular in said plane.

8. The trephination apparatus of claim 1 wherein said through-aperture is further defined as extending between a first end and a second end, said second end at said plane with said second opening, and having said female profile between said first end and said second end.

9. The trephination apparatus of claim 1 wherein said blade is further defined as moveably mounted on said second member and moveable between a retracted position and an extended position, said first cutting edge positioned between said first end and said plane when said blade is in said retracted position, and said plane between at least part of said first cutting edge and said first end and when said blade is in said extended position.

10. The trephination apparatus of claim 9 further comprising:
at least one spring positioned between said second member and said blade and biasing said blade to said retracted position.

11. The trephination apparatus of claim 1 wherein said first cutting edge has an undulated profile.

12. The trephination apparatus of claim 1 further comprising:
at least one vacuum connectable with at least one of said first opening and said third opening to draw air through one of said first internal chamber and said second internal chamber to generate a vacuum in one of said first internal chamber and said second internal chamber when said fourth opening or said sixth opening is abutting another structure and thereby closed.

13. The trephination apparatus of claim 1 further comprising:
a cutting tool having:
a second body sized to be received in said through-aperture when said blade and said second member are not positioned in said through-aperture,
a shaft positioned in said second body and configured to rotate relative to said second body,
an arm mounted on and projecting away from said shaft, and
a second cutting edge mounted on said arm.

14. The trephination apparatus of claim 13 wherein:
said first member extends along said aperture axis between a first end and a second end, said second end at said plane with said second opening; and
said cutting tool further comprises at least one protuberance projecting further away from said aperture axis than said second body when said second body is received in said through-aperture, said protuberance abutting said first end when said second body is received in said through-aperture and limiting movement of said second body into said through-aperture.

15. The trephination apparatus of claim 13 wherein said shaft is further defined as mounted in said second body for rectilinear movement along said aperture axis when said second body is received in said through-aperture, whereby said arm and said second cutting edge are also rectilinearly moveable along said aperture axis.

16. The trephination apparatus of claim 15 wherein:
said shaft is further defined as moveable between a retracted position and an extended position;
said second body further defines:
a bottom edge positionable in said plane when said second body is received in said through-aperture, a cavity recessed from said bottom edge shaped to correspond to a shape of said arm and of said second cutting edge, whereby said arm and said second cutting edge are received in said cavity when said shaft is in said retracted position and are spaced from said cavity when said shaft is in said extended position; and said second cutting edge is configured to abut said first member in said plane when (a) said second body is received in said through-aperture, (b) said shaft is rectilinearly spaced from said retracted position, and (c) said second cutting edge is rotated about said aperture axis away from said cavity.

17. The trephination apparatus of claim 13 wherein said second cutting edge is further defined as directed along said aperture axis when said second body is received in said through-aperture.

18. The trephination apparatus of claim 13 wherein said second cutting edge is further defined as directed transverse to said aperture axis when said second body is received in said through-aperture.

19. A method of using the trephination apparatus of claim 13 to treat an eye of a patient receiving a donor cornea comprising:
placing the first member on the cornea whereby the fourth opening is closed by the cornea;
applying a suction to the first opening to create a vacuum in the first internal chamber and selectively grasp a portion of the recipient's cornea;
inserting the second body of the cutting tool into the through-aperture until the second body rests on the first member;
moving the shaft relative to the second body, rectilinearly downward along the aperture axis, to space the arm and the second cutting edge from the second body;
rotating the shaft relative to the second body, about the aperture axis, to position the second cutting edge under a portion of the recipient's cornea and under a portion of the first member; and
moving the shaft relative to the second body, rectilinearly upward along the aperture axis, to pierce the recipient's cornea with the second cutting edge.

20. A method using the trephination apparatus of claim 1 to remove a portion of a cornea of an eye comprising:
placing the first member on the cornea whereby the fourth opening is closed by the cornea;
inserting the first body of the second member into the through-aperture and on the cornea, whereby the sixth opening is closed by the cornea;
applying a suction to the first opening and the fifth opening to create a vacuum in the first internal chamber and the second internal chamber; and
moving the blade along the aperture axis in a space between the first member and the second member until the blade pierces the cornea and detaches the portion from a remainder of the cornea.

* * * * *